United States Patent
Kado et al.

(10) Patent No.: US 10,472,235 B2
(45) Date of Patent: Nov. 12, 2019

(54) SYNTHESIS GAS MANUFACTURING METHOD AND SYNTHESIS GAS MANUFACTURING APPARATUS

(71) Applicants: CHIYODA CORPORATION, Yokohama-shi, Kanagawa (JP); Japan Oil, Gas and Metals National Corporation, Tokyo (JP)

(72) Inventors: Shigeru Kado, Yokohama (JP); Kohei Urasaki, Yokohama (JP); Kyoji Ishikawa, Yokohama (JP); Hironori Kawai, Yokohama (JP); Yusuke Nakajima, Yokohama (JP)

(73) Assignees: CHIYODA CORPORATION, Yokohama-shi, Kanagawa (JP); JAPAN OIL, GAS AND METALS NATIONAL CORPORATION, Tokyo (JP)

( * ) Notice: Subject to any disclaimer, the term of this patent is extended or adjusted under 35 U.S.C. 154(b) by 187 days.

(21) Appl. No.: 15/558,246

(22) PCT Filed: Mar. 23, 2016

(86) PCT No.: PCT/JP2016/001657
§ 371 (c)(1),
(2) Date: Sep. 14, 2017

(87) PCT Pub. No.: WO2016/152151
PCT Pub. Date: Sep. 29, 2016

(65) Prior Publication Data
US 2018/0093886 A1    Apr. 5, 2018

(30) Foreign Application Priority Data

Mar. 23, 2015    (JP) .................................. 2015-059106

(51) Int. Cl.
*C01B 3/26* (2006.01)
*B01J 23/63* (2006.01)
(Continued)

(52) U.S. Cl.
CPC ............... *C01B 3/26* (2013.01); *B01J 8/0207* (2013.01); *B01J 8/0242* (2013.01); *B01J 8/0411* (2013.01);
(Continued)

(58) Field of Classification Search
CPC .............. C01B 3/26; C01B 2203/0261; C01B 2203/1011; C01B 3/386; C01B 32/40;
(Continued)

(56) References Cited

U.S. PATENT DOCUMENTS 7,226,567 B1 * 6/2007 Olbert .................... B01J 8/067
422/653
2008/0184892 A1   8/2008 Boersma et al.
2008/0210596 A1   9/2008 Litt et al.

FOREIGN PATENT DOCUMENTS

JP    2001-89108 A    4/2001
JP    2005-187460 A   7/2005
(Continued)

OTHER PUBLICATIONS

International Search Report dated Jun. 7, 2016, issued in counterpart application No. PCT/JP2016/001657, w/English translation. (5 pages).
(Continued)

*Primary Examiner* — Anthony J Zimmer
(74) *Attorney, Agent, or Firm* — Westerman, Hattori, Daniels & Adrian, LLP (57) ABSTRACT

A method of manufacturing synthesis gas by catalytic partial oxidation can prevent formation of hot spots from taking place when driving mixture gas to pass through a catalyst-filled layer at high velocity. The method comprises convert-
(Continued)

ing mixture gas of source gas containing lower hydrocarbons and oxidative gas containing oxygen into synthesis gas containing hydrogen and carbon monoxide as main components thereof by causing mixture gas to flow through a fixed bed catalyst layer arranged in a reactor. The method of manufacturing synthesis gas by catalytic partial oxidation is conducted such that the mixture gas is made to flow to the catalyst layer under the condition that the Reynolds number does not exceed 20 at the inlet of the catalyst layer.

6 Claims, 5 Drawing Sheets

(51) Int. Cl.
| | |
|---|---|
| B01J 35/04 | (2006.01) |
| C01B 32/40 | (2017.01) |
| B01J 12/00 | (2006.01) |
| B01J 19/24 | (2006.01) |
| C07C 9/04 | (2006.01) |
| B01J 37/08 | (2006.01) |
| B01J 23/56 | (2006.01) |
| B01J 35/02 | (2006.01) |
| B01J 37/00 | (2006.01) |
| B01J 37/02 | (2006.01) |
| B01J 8/02 | (2006.01) |
| B01J 8/04 | (2006.01) |
| C01B 3/38 | (2006.01) |
| B01J 35/00 | (2006.01) |
| B01J 23/46 | (2006.01) |
| B01J 32/00 | (2006.01) |

(52) U.S. Cl.
CPC .............. *B01J 12/00* (2013.01); *B01J 12/007* (2013.01); *B01J 19/244* (2013.01); *B01J 19/248* (2013.01); *B01J 19/249* (2013.01); *B01J 19/2485* (2013.01); *B01J 19/2495* (2013.01); *B01J 23/464* (2013.01); *B01J 23/56* (2013.01); *B01J 23/63* (2013.01); *B01J 35/0006* (2013.01); *B01J 35/023* (2013.01); *B01J 35/04* (2013.01); *B01J 37/0018* (2013.01); *B01J 37/0201* (2013.01); *B01J 37/0215* (2013.01); *B01J 37/082* (2013.01); *B01J 37/088* (2013.01); *C01B 3/386* (2013.01); *C01B 32/40* (2017.08); *C07C 9/04* (2013.01); *B01J 32/00* (2013.01); *B01J 2208/00672* (2013.01); *B01J 2208/024* (2013.01); *B01J 2208/025* (2013.01); *B01J 2219/00263* (2013.01); *B01J 2523/00* (2013.01); *C01B 2203/0261* (2013.01); *C01B 2203/1011* (2013.01); *C01B 2203/1064* (2013.01)

(58) Field of Classification Search
CPC ................ C01B 2203/1064; C07C 9/04; B01J 2219/00263; B01J 2208/025; B01J 2208/024; B01J 2208/00672; B01J 2523/00; B01J 32/00; B01J 23/464; B01J 35/0006; B01J 8/0411; B01J 8/0242; B01J 8/0207; B01J 19/249; B01J 19/2485; B01J 19/248; B01J 12/007; B01J 19/2495; B01J 37/0215; B01J 37/0201; B01J 37/0018; B01J 35/023; B01J 23/56; B01J 37/088; B01J 37/082; B01J 19/244; B01J 12/00; B01J 35/04; B01J 23/63
See application file for complete search history.

(56) References Cited

FOREIGN PATENT DOCUMENTS

| | | |
|---|---|---|
| JP | 2005-199264 A | 7/2005 |
| JP | 2005-255431 A | 9/2005 |
| JP | 2006-21943 A | 1/2006 |
| JP | 2009-29680 A | 2/2009 |
| JP | 2010-516843 A | 5/2010 |
| JP | 2010-517916 A | 5/2010 |

OTHER PUBLICATIONS

Bitsch-Larsen et al., "Catalytic partial oxidation of methane on rhodium and platinum: Spatial profiles at elevated pressure", Applied Catalysis A: General, 348, 2008, pp. 165-172, cited in Specification (8 pages).
International Preliminary Report on Patentabiligy (Form PCT/IB/373) issued in counterpart International Application No. PCT/JP2016/001657, with Form PCT/ISA/237. (9 pages).

* cited by examiner

FIG. 1

GRANULE CATALYST

FIG. 2

FOAM CATALYST

SYNTHESIS GAS MANUFACTURING METHOD AND SYNTHESIS GAS MANUFACTURING APPARATUS

TECHNICAL FIELD

The present invention relates to a method of manufacturing synthesis gas from lower hydrocarbons such as natural gas by means of a catalytic partial oxidation technique and an apparatus to be used for the method.

BACKGROUND ART

Natural gas contains as main components thereof lower hydrocarbons (having 1 to 5 carbon atoms in a molecule as far as this application is concerned), of which methane is a typical one. In recent years, techniques for manufacturing synthesis gas containing hydrogen and carbon monoxide as main components thereof from natural gas have been developed and improved to a great extent. Synthesis gas serves as source material for manufacturing various products by means of C1-chemistry and also as source material for manufacturing clean fuels such as methanol, synthetic gasoline and dimethyl ether (DME) and hence the reforming technology of producing synthesis gas from natural gas is an important technology that provides the basis for effective utilization of natural gas.

Known reforming techniques for producing synthesis gas from natural gas include steam reforming, auto thermal reforming (ATR) and catalytic partial oxidation (CPDX), of which steam reforming is a technique of converting natural gas into synthesis gas that contains hydrogen and carbon monoxide as main components thereof by adding steam to natural gas and causing the steam-added natural gas to pass through a reaction tube arranged in a heating furnace and filled with a reforming catalyst. However, this technique is accompanied by a problem that the above described reaction is an endothermic reaction and thermal energy needs to be massively supplied to the reaction system from outside and that a gigantic reaction apparatus is required to manufacture synthesis gas on a large scale by means of this technique. ATR, on the other hand, is a technique of burning part of the natural gas that is supplied as source gas by means of a burner with oxygen or air added thereto and causing the carbon dioxide and the moisture (steam) existing in the produced hot combustion gas to react with the unburned methane remaining in the source natural gas in a reforming catalyst layer. This technique provides an advantage that the heat generated as a result of the combustion reaction is utilized in the reforming reaction (which is an endothermic reaction) so that no thermal energy is required to be supplied from outside. However, this technique is accompanied by a problem that an upper part of the catalyst layer is exposed to hot gas and hence it can easily be degraded and additionally that the reaction system can hardly be run under economically optimal conditions because steam needs to be supplied excessively for the purpose of prolonging the service life of the burner.

Finally, CPDX is a technique obtained by replacing the combustion process of using a burner of ATR with a combustion process of using a catalyst. The practical advantage of CPDX lies in that a combustion reaction and a reforming reaction are conducted simultaneously and concurrently so that it can prevent only an upper part of the catalyst layer from becoming excessively hot unlike ATR where a combustion reaction and a reforming reaction are conducted sequentially and stepwise. However, to make this technique feasible, it is necessary to either realize "direct catalytic partial oxidation (D-CPDX)" of suspending the process of burning the lower hydrocarbons in the source natural gas at the stage where the lower hydrocarbons are oxidized to produce hydrogen and carbon monoxide so that the lower hydrocarbons may not be completely burnt out to produce carbon dioxide and moisture or develop a catalyst that can make a combustion reaction and a reforming reaction proceed simultaneously and concurrently. In the past, the inventors of the present invention succeeded in developing such a catalyst and paving a way to practical realization of CPDX (see PTL 1).

CITATION LIST

Patent Literature

PTL 1: Japanese Patent Application Laid-Open No. 2005-199264
PTL 2: Japanese Patent Application Laid-Open No. 2005-187460
PTL 3: Japanese Patent Application Laid-Open No. 2005-255431
PTL 4: Japanese Patent Application Laid-Open No. 2009-029680

Non Patent Literature

NPL 1: Applied catalysis A: General, 348, (2008), 16.

SUMMARY OF INVENTION

Technical Problem

With the above described CPDX technique (the D-CPDX technique in particular), gas is made to flow through a catalyst layer at a very high space velocity so that this technique provides an advantage of remarkably downsizing the reactor if compared with the preceding techniques of steam reforming and ATR. It was, however, found that, as the velocity at which gas passes through the catalyst layer is raised, hot spots are formed in the catalyst layer to give rise to a problem that the formed hot spots can consequently degrade and destroy the catalyst.

The problem of formation of hot spots is originating from the problem that the combustion reaction precedes the reforming reaction to consequently heat an upper part of the catalyst layer to very high temperatures. Then, as a result, hot spots are produced there. It is known that a similar problem is observed in scenes other than those of manufacturing synthesis gas by reforming natural gas. For example, it is known that a similar problem arises in unsaturated aldehydes manufacturing processes and also in unsaturated carboxylic acids manufacturing processes that utilize vapor phase catalytic oxidation of olefins. As a measure for solving the problem, there has been proposed an apparatus in which a catalyst whose catalytic activity is suppressed is arranged at the inlet part thereof where hot spots are apt to be formed and then other catalysts are arranged to follow the first one such that their catalytic activities are increased stepwise toward the outlet part of the apparatus (see PTL 2). As another measure for solving the problem, there has been proposed a radial flow type reaction apparatus devised to introduce shift gas deep into the catalyst layer by extending the gas feed pipe (distribution pipe) in the catalyst layer as a reactor for selectively oxidizing the carbon monoxide remaining in the shift gas to produce carbon dioxide in a process of manufacturing hydrogen gas to be used for fuel cells (see PTL 3).

However, the problem of formation of hot spots with CPDX (D-CPDX in particular) is a problem that arises as reactive gas is forced to pass through a catalyst layer at a high velocity and therefore the problem can highly likely arise as a combustion reaction proceeds prior to a reforming reaction on the catalyst surface even if the combustion reaction in the vapor phase is suppressed. Thus, the techniques proposed in Patent Literature 2 and in Patent Literature 3 are practically not effective at all to solve the above identified problem. When the technique proposed in Patent Literature 2 is applied to CPDX, it will end up with an adverse effect because perfect combustion can proceed on the low activity catalyst arranged at and near the inlet part of the reaction apparatus. Above all, the measure proposed in Patent Literature 2 might have ignored the purpose of the D-CPDX method of causing a combustion reaction and a reforming reaction to proceed simultaneously and concurrently. Furthermore, it inerasably entails an apprehension about the risk of damaging the economic advantages of D-CPDX due to the use of an increased amount of catalyst. The measure proposed in Patent Literature 3 is introducing source gas in a dispersive manner in the depth direction of the catalyst layer and hence this measure can randomly produce hot spots not only in an upper part of the catalyst layer but in the entire area of the catalyst layer. Additionally, with synthesis gas manufacturing, hydrogen and carbon monoxide that are more reactive than the source material of hydrocarbons are produced as the reaction proceeds and therefore, if oxidative gas such as oxygen is introduced in such an environment, the combustion reaction of hydrogen and carbon monoxide proceeds in advance to expectedly reduce the synthesis gas manufacturing efficiency.

With the CPDX technique, additionally, it is necessary to remind that this technique handles mixture gas of lower hydrocarbons and oxygen-containing gas, which can explode once it is ignited. As a technique for avoiding explosion, it has been proposed to prevent flames from running backward toward the upstream side by filling the mixer for mixing gas that typically contains methane and oxygen-containing gas with inactive particles and making the gas flow velocity in narrow flow path parts in the layer that is filled with the inactive particles not lower than the combustion speed (the flame propagation velocity) (see PTL 4). However, this technique is developed simply by paying attention to prevention of explosion of mixture gas on the way thereof for getting to the catalyst-filled layer in the reactor and the problem of formation of hot spots in the catalyst-filled layer is totally neglected. Additionally, this technique is accompanied by a problem of unnecessarily increasing the differential pressure in the reactor.

In view of the above identified problems of the known techniques, it is therefore an object of the present invention to provide a method of preventing hot spots from being formed when mixture gas is driven to flow at high velocity in a catalyst-filled layer with the catalytic partial oxidation method (CPDX method, D-CPDX method in particular) of manufacturing synthesis gas containing hydrogen and carbon monoxide as main components thereof by partially oxidizing gas containing lower hydrocarbons such as natural gas (source gas) with oxygen-containing gas (oxidative gas).

Another object of the present invention is to provide a method of preventing mixture gas of flammable source gas that contains lower hydrocarbons and oxygen-containing gas from exploding on the way thereof for getting to a catalyst-filled layer besides the above object of preventing hot spots from being formed in the catalyst-filled layer.

Still another object of the present invention is to provide a synthesis gas manufacturing apparatus that is suited for executing the above described methods.

Further objects of the present invention will become apparent from the description of the invention that is specifically given below.

Solution to Problem

In an aspect of the present invention, the above identified problems are solved by providing a method of manufacturing synthesis gas by catalytic partial oxidation, comprising causing mixture gas of source gas containing lower hydrocarbons and oxidative gas containing oxygen to flow through a fixed bed catalyst layer in a reactor and thereby converting the mixture gas into synthesis gas containing hydrogen and carbon monoxide as main components thereof, characterized in that the mixture gas is caused to flow through the catalyst layer under a condition where the Reynolds number does not exceed 20 at the inlet of the catalyst layer.

Preferably, the method is conducted such that the gas flow velocity of the mixture gas in a mixture gas feed flow path reaching to the catalyst layer is not less than the critical burning velocity.

In another aspect of the present invention, the above identified problems are solved by providing a reactor for manufacturing synthesis gas, comprising a pressure vessel and a fixed bed catalyst layer arranged in the pressure vessel, the reactor being configured to cause mixture gas of source gas containing lower hydrocarbons and oxidative gas containing oxygen to flow through the catalyst layer, the mixture gas being supplied through a mixture gas feed flow path reaching to the catalyst layer, characterized in that the equivalent diameter R of the mixture gas feed flow path satisfies the requirement of the formula below:

$$R \leq (8F/\pi K)^{1/3}$$

where
F represents the feed flow rate of mixture gas;
K represents the velocity gradient defined as $K=2V/R$ (V representing the critical burning velocity); and
n represents the circle ratio.

Preferably, the reactor has a reaction area that makes the Reynolds number not greater than 20 at the inlet of the catalyst layer, where "the reaction area" is the (total) cross sectional area of the mixture gas flow flowing in perpendicularly relative to the catalyst layer, or the total sum of the cross sectional areas of the inlet side surfaces of the component catalyst layers arranged in parallel relative to the incoming mixture gas.

Advantageous Effects of Invention

According to the present invention, in a process of manufacturing synthesis gas containing hydrogen and carbon monoxide as main components thereof by partially oxidizing gas containing lower hydrocarbons with oxygen-containing gas by means of catalytic partial oxidation (CPDX, D-CPDX in particular), formation of hot spots that arises when mixture gas is caused to flow through a catalyst-filled layer at a high velocity can effectively be prevented from taking place. Additionally, the process of manufacturing synthesis gas can be executed under conditions that can avoid the risk of explosion on the way for mixture gas to get to the catalyst-filled layer while effectively preventing formation of hot spots from taking place.

DESCRIPTION OF EXAMPLES

The present invention is to pay attention to the flow of mixture gas in a catalyst layer. In an aspect, the present invention is essentially characterized in that mixture gas is caused to flow through the catalyst layer of a reactor under a condition that the Reynolds (Re) number at the inlet part of the catalyst layer does not exceed 20. The present invention is also to pay attention to the flow of mixture gas in the mixture gas feed path reaching to the catalyst layer. In other words, the present invention is also essentially characterized in that mixture gas is fed to the catalyst layer under a condition that the gas flow velocity in the feed path is not less than the critical burning velocity of the mixture gas.

The Reynolds number is a well-known index in the field of chemical engineering that deals with gas flows in apparatus. It is a dimensionless number expressing the ratio of the contribution of inertial force to the contribution of viscous force in a flow in question (and hence the relative magnitude relationship thereof). The Reynolds number is defined by the mathematical formula shown below.

$$Re = \rho u d / \mu, \quad \text{(Mathematical formula 1)}$$

where
Re is the Reynolds number;
$\rho$ is the density (kg/m$^3$) of the fluid;
u is the flow velocity (m/s);
d is the representative length (m) of the apparatus; and
$\mu$ is the viscosity (Pa·s) of the fluid.
Of the above quantities, while the density $\rho$ and the viscosity $\mu$ vary as a function of the temperature and the pressure of the fluid, they are unequivocally determined once constant values are given to the temperature and the pressure respectively. While the flow velocity $\mu$ may vary depending on the position in the catalyst layer when looked into microscopically, the average flow velocity can be obtained by dividing the superficial flow velocity, which is determined by dividing the feed flow rate of mixture gas by the reaction area, by the porosity. However, since the representative length d cannot necessarily unequivocally be defined, it needs to be defined each time when the Reynolds number is to be determined.

Figure 1:
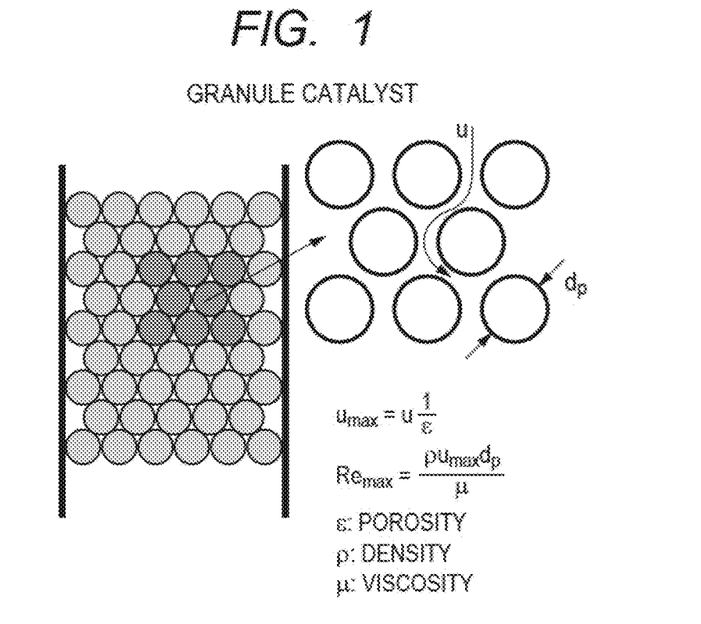
FIG. 1 is a schematic illustration of a catalyst layer formed by filling a column with a particulate catalyst.
Figure 2:
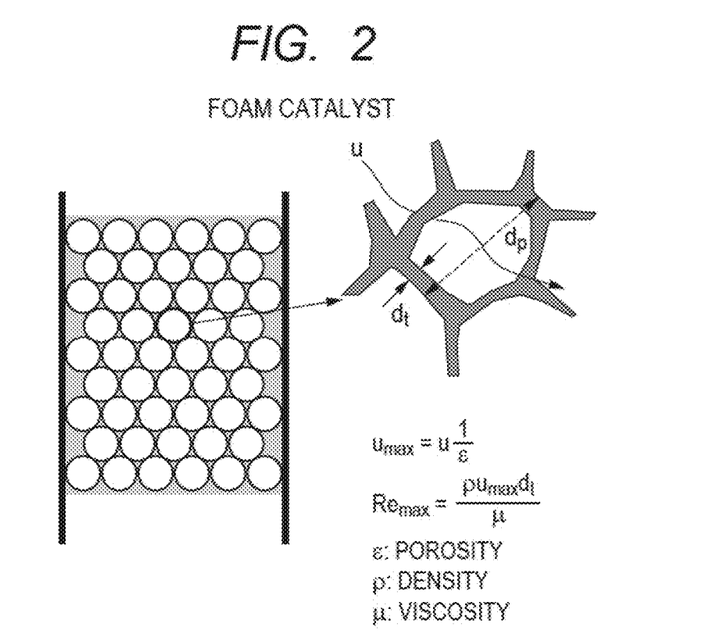
FIG. 2 is a schematic illustration of a catalyst layer formed by filling a column with a molded body of foam catalyst.

While various different forms of catalyst layers can be used with catalytic partial oxidation, catalyst layers that can be used with catalytic partial oxidation can roughly be classified into two groups. FIG. 1 shows a typical catalyst layer belonging to one of the groups, where fluid is forced to flow through the voids among the particles filled in the catalyst layer and FIG. 2 shows a typical catalyst layer belonging to the other one of the groups, where fluid is forced to flow through open cells. For the purpose of the present invention, the average particle size $d_p$ of the filler particles is adopted as the representative length for the former group, whereas the average thickness (skeleton diameter) $d_t$ of the partition walls between cells is adopted as the representative length for the latter group. In either instance, a dimensional value of the filler substance (solid) is employed for the representative length. Thus, the two groups including the one where the filler substance is of the filler particle type and the other where the filler substance is of the open cell structure type can be handled in the unified manner by defining the representative length in the above described manner.

Regardless if the filler substance of the catalyst layer is of the filler particle type or of the open cell structure type, preferably a catalyst carrying layer (carrier layer) is arranged on a heat-resistant support which is typically made of a ceramic material and the catalyst metal is carried on the carrier layer. The ceramic material of the support can suitably be selected from alumina, silica, titania, zirconia, zircon, yttrium and mullite among others. The material of the carrier layer is preferably and generally a metal oxide. Particularly preferably, the material of the carrier layer is a mixture of a first component, which is an oxide of any of the Group IIA elements such as magnesium and calcium, a second component, which is an oxide of cerium, praseodymium or terbium, and a third component, which is zirconia or calcia-stabilized zirconia. The catalyst metal is preferably a metal of Group VIII. Particularly preferably, the catalyst metal is rhodium.

Figure 3:
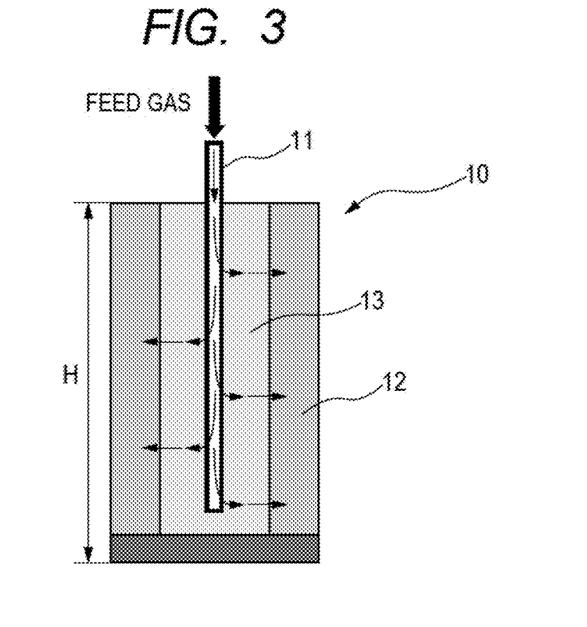
FIG. 3 is a schematic illustration of a catalyst layer unit of a radial flow reactor.
Figure 4:
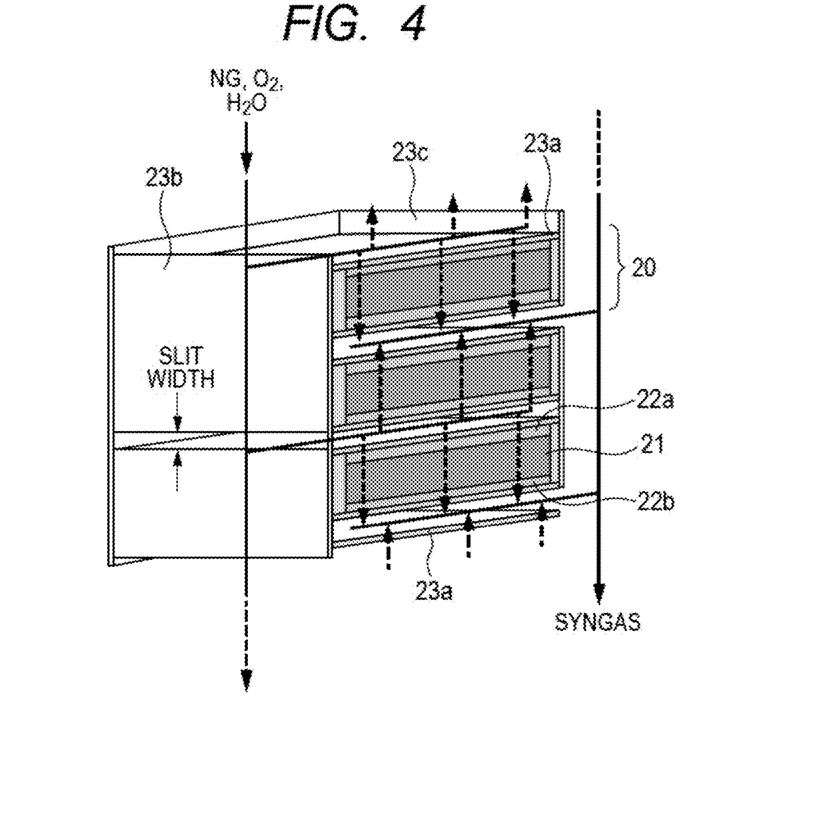
FIG. 4 is a schematic illustration of a laminate of catalyst layer units of a plate reactor.

As the filler substance of the catalyst layer, a particulate substance may be filled in the reactor as it is, although the voids in the catalyst layer can easily be made to show a uniform size when the molded predetermined shape substance is filled in the reactor. Particularly, in the instance of using foam filler, normally, filler molded to show a profile that matches the profile of the internal space of the reactor is filled in the reactor. Such molded filler is referred to as porous monolith and, a porous monolith to be used for the purpose of the present invention is ceramic foam having a web-like structure of 10 to 40 cells per inch or a ceramic honeycomb having a honeycomb structure of 100 to 400 cells per square inch. When such porous monolithic filler is employed, the gap between the filler and the inner wall of the reactor is preferably filled with a sealing material in order to prevent gas from slipping through the gap due to a wall effect. When porous monolithic filler is employed for the catalyst layer, the porosity of the porous monolithic filler is much greater if compared with an instance where the reactor is filled with a particulate catalyst, so that the reactor can be made to be a structure having a small representative length (d). Then, as a result, the use of porous monolithic filler provides an advantage of making the Re number small if the superficial velocity of feed gas is increased so that hot spots are hardly produced in the reactor. Moreover, the use of porous monolithic filler provides an additional advantage of producing only low differential pressure even if the gas linear velocity is increased. While the mode of gas flow in the reactor is not subjected to any particular limitations, a mode of flow (radial flow type flow) that is produced when the reactor is filled with a cylindrical catalyst layer and gas is driven to flow from the center toward the circumference (or vice versa) as shown in FIG. 3 and a mode of flow (plate type flow) that is produced when a plurality of units of plates, each of which is formed by a plate-shaped catalyst unit layer and a pair of gas permeable plates sandwiching the plate-shaped catalyst unit layer, are arranged in a manner as shown in FIG. 4 are particularly preferable.

Now, the present invention will be described in greater detail by way of specific Examples. Note, however, that the Examples of the present invention that will be described hereinafter do not limit the scope of the present invention at all and they are only currently preferable Examples of the present invention.

EXAMPLE 1

The inventors of the present invention conducted an experiment of preparing a molded foam catalyst object by coating a cylindrical piece of ceramic foam with a catalyst carrier material, making the coated piece of ceramic foam carry rhodium (Rh) thereon, forming a catalyst layer by filling a tubular column with the prepared cylindrical foam piece of catalyst as shown in FIG. 2 and then causing mixture gas of town gas and oxygen to flow through the catalyst layer so as to produce synthesis gas. The inventors of the present invention then repeated the experiment for eleven times (RUN1 through 11), slightly changing the experiment conditions for each run. The obtained synthesis gas was sampled from time to time in a timely manner to trace the change in the reaction performance of the catalyst. Additionally, the used catalyst was drawn out and the physically degraded state of the catalyst was observed. In this way, the inventors of the present invention determined if the experiments were run in a stable manner with least degradation of the catalyst or not. Table 1 shows the conditions of the experiments and Table 2 shows the results of the experiments.

Figure 5:
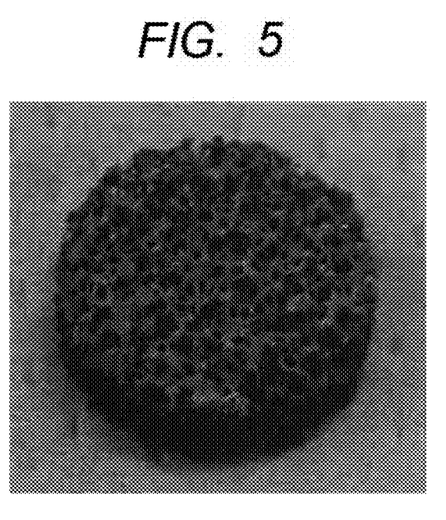
FIG. 5 is a view of the foam catalyst after the test of RUN1 in Table 1.
Figure 6:
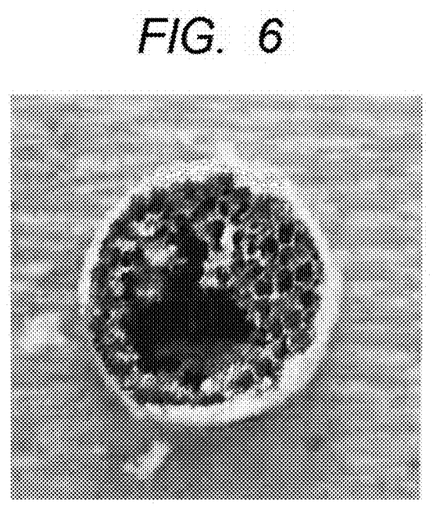
FIG. 6 is a view of the foam catalyst after the test of RUN6 in Table 1.

FIG. 5 shows how the foam catalyst appeared after the experiment of RUN1 listed in Table 1. As seen from the results of RUN1 in Table 2, the rate of change of the conversion ratio (the rate of change with time of the ratio of the volume of hydrocarbons that reacted with oxygen relative to the total volume of hydrocarbons in the supplied town gas) stably remained at about 0.01%/h and no damage was observed in the drawn out catalyst. On the other hand, FIG. 6 shows how the foam catalyst appeared after the experiment of RUN6 listed in Table 1. As shown in FIG. 6, the skeleton of the ceramic foam had been molten to produce a large hole due to formation of hot spots. As seen from the results of RUN 6 in Table 2, the rate of change of the conversion ratio was 0.02%/h. On the basis of these results, the inventors of the present invention determined that catalyst degradation took place when the rate of change of the conversion ratio fell by not less than 0.02%/h mainly because of formation of hot spots.

(1-1) Preparation of Molded Foam Catalyst Objects

Ceramic foams of 20 cells/inch (about 8 cells/cm, cell diameter: 1.27 mm), 30 cells/inch (about 12 cells/cm, cell diameter: 0.85 mm), 34 cells/inch (about 13.5 cells/cm, cell diameter: 0.75 mm) and 40 cells/inch (about 16 cells/cm, cell diameter: 0.64 mm) were used for the respective molded foam catalyst objects. The skeletons showed a constant skeleton diameter d ($d_t$) regardless of cell diameter so long as the cell diameter was found within the above described range. As a result of microscopic observations, the skeleton diameter was found to be 0.1 mm. Each of the molded objects was coated with a catalyst carrier material and made to carry rhodium. The prepared molded foam catalyst objects were then employed as so many foam catalysts. The catalyst carrier material that was used for coating was $CeO_2$—$ZrO_2$—MgO-based powder. More specifically, the $CeO_2$—$ZrO_2$—MgO-based powder was prepared by mixing cerium hydroxide, zirconium hydroxide and magnesium hydroxide at a ratio of $CeO_2/ZrO_2/MgO=1/1/1$ (weight ratio) and graphite was added to the mixture by 5 wt % and then mixed well. The obtained mixture was then subjected to a compression molding operation and the molded product was calcined at 1,200° C. for 6 hours. Subsequently, the calcined molded product was crushed to powder. Then, water was added to the obtained powder to turn it into slurry. Each of the ceramic foams was coated with the slurry at a ratio of 15 to 20 wt % relative to the ceramic foam and the coated ceramic foam was calcined to obtain a catalyst carrier. The obtained catalyst carrier was then made to carry rhodium by impregnating the catalyst carrier with aqueous solution of rhodium acetate and drying and calcining the impregnated catalyst carrier. The catalyst carrier was made to carry Rh by 1 wt %.

(1-2) Manufacturing of Synthesis Gas

Catalyst layers were prepared by filling tubular columns respectively with the molded foam catalyst objects of the different cell diameters prepared in the above (1-1). The gap between each of the molded catalyst objects and the inner wall of the corresponding one of the tubular columns was filled with heat-insulating wool in order to prevent gas from slipping through the gap. Synthesis gas was manufactured by causing mixture gas containing town gas ($CH_4/C_2H_6/C_3H_8/C_4H_{10}$=89.5/6.0/2.8/1.6) and oxygen at an O/C ratio of between 0.9 and 1.0 to flow through each of the catalyst layers at a temperature of 250° C. under variable pressure and at variable flow velocity. Table 1 shows the conditions of the experiments. For each of the experiments, the gas flow rate (GHSV) was determined by dividing the total amount of the supplied gas (as reduced to 0° C. and 1 atm) by the volume of the catalyst. The gas flow velocity u was the flow velocity under the reaction conditions at the inlet of the catalyst layer, which was computationally determined from the porosity of the catalyst layer, the temperature at the inlet of the catalyst layer and the pressure also at the inlet. The temperature at the inlet of the catalyst layer was determined by referring to the results obtained by measuring the temperature distribution of the catalyst layer during a CPDX reaction process by means of capillary sampling as shown in NPL 1. The average density p and the average viscosity μ were the arithmetic average values of the density and the viscosity of each of the components of the mixture gas under the catalyst layer inlet pressure and at the catalyst layer inlet temperature and weighting them with the abundance ratio. The Reynolds number was determined by calculations using the formula of Re=ρud/μ.

(1-3) Results

Table 2 summarily shows the results of the experiments. The carbon conversion ratio of each of the experiments was determined by analyzing the gas obtained at the outlet of the catalyst layer and using the definitional equation shown below.

carbon conversion ratio=(total amount of carbon in supplied hydrocarbons [mol/h]−methane runoff [mol/h])/(total amount of carbon in supplied hydrocarbons (mol/h))

The changing rate of the conversion ratio (%/h) was determined by dividing the difference between the carbon conversion ratio 20 minutes after the start of the reaction and the carbon conversion ratio after the elapse of the predetermined reaction time by the predetermined reaction time. The manufacturing of synthesis gas was evaluated as stable (○) when the changing rate of the conversion ratio was less than 0.02%/h, whereas the manufacturing of synthesis gas was evaluated as unstable (x) when the changing rate of the conversion ratio was not less than 0.02%/h because degradation of the catalyst was in progress mainly due to generation of hot spots.

TABLE 1

| RUN No. | Skeleton diameter d (mm) | Gas flow velocity u (m/s) | Average density ρ (kg/m³) | Average viscosity μ (μPa · s) | Re Number ρud/μ (—) | Reaction area (cm²) |
|---|---|---|---|---|---|---|
| 1 | 0.1 | 0.43 | 3.95 | 31.36 | 5.37 | 2.0 |
| 2 | 0.1 | 0.44 | 3.92 | 31.29 | 5.48 | 2.0 |
| 3 | 0.1 | 0.65 | 3.97 | 31.50 | 8.15 | 2.0 |
| 4 | 0.1 | 0.60 | 5.89 | 31.38 | 11.24 | 2.0 |
| 5 | 0.1 | 1.35 | 3.95 | 31.36 | 16.98 | 0.6 |
| 6 | 0.1 | 1.40 | 6.25 | 31.25 | 28.02 | 0.6 |
| 7 | 0.1 | 0.74 | 6.15 | 31.10 | 14.71 | 0.6 |
| 8 | 0.1 | 0.83 | 6.17 | 31.13 | 16.38 | 0.6 |
| 9 | 0.1 | 0.91 | 6.19 | 31.16 | 18.04 | 0.6 |
| 10 | 0.1 | 1.38 | 6.28 | 31.30 | 27.67 | 0.6 |
| 11 | 0.1 | 0.69 | 8.12 | 31.36 | 18.04 | 0.6 |

TABLE 2

| RUN No. | Carbon conversion ratio 20 min after start of reaction % | Reaction time (h) | Carbon conversion ratio after elapse of reaction time (%) | Changing rate of conversion ratio (%/h) | stability |
|---|---|---|---|---|---|
| 1 | 84.3 | 44 | 83.7 | 0.01 | ○ |
| 2 | 86.0 | 2000 | 84.6 | 0.00 | ○ |
| 3 | 77.7 | 18 | 77.6 | 0.01 | ○ |
| 4 | 75.9 | 20 | 75.8 | 0.00 | ○ |
| 5 | 86.0 | 141 | 85.8 | 0.00 | ○ |
| 6 | 83.8 | 41 | 82.9 | 0.02 | X |
| 7 | 83.1 | 1030 | 82.6 | 0.00 | ○ |
| 8 | 84.2 | 20 | 84.0 | 0.01 | ○ |
| 9 | 84.0 | 22 | 83.7 | 0.01 | ○ |
| 10 | 86.1 | 41 | 84.5 | 0.04 | X |
| 11 | 81.8 | 40 | 81.8 | 0.00 | ○ |

(1-4) Inventors' Comment

From Table 2, it can be seen that hot spots are produced and the reaction performance of the catalyst falls when the synthesis gas manufacturing process is run under the condition of a Re number greater than 20.

EXAMPLE 2

The operation conducted for this Example was the same as that of Example 1 except that the catalyst layers of this Example were formed by preparing particulate catalysts instead of the foam molded catalyst objects of Example 1 and filling them in the respective columns as shown in FIG. 1.

(2-1) Preparation of Particulate Catalysts

Each of the catalysts was prepared by crushing a catalyst carrier formed by compression molding and sieving the crushed catalyst carrier to produce particulate catalysts of two different particle sizes including A) those having a particle size between 0.35 and 0.43 mm (average particle size: 0.39 mm) and B) those having a particle size between 0.85 and 1.18 mm (average particle size: 1.02 mm), which were then put to use. The catalyst carrier, which was $CeO_2$—$ZrO_2$—MgO, was prepared in a manner similar to the one in which the $CeO_2$—$ZrO_2$—MgO-based powder was formed and used for coating a foam catalyst for Example 1. The obtained catalyst carrier was made to carry rhodium by impregnating the catalyst carrier with aqueous solution of rhodium acetate and drying and calcining the impregnated catalyst carrier. The rhodium (Rh) concentration was made to be equal to 0.2 wt %.

(2-2) Manufacturing of Synthesis Gas

Catalyst layers were prepared by filling tubular columns respectively with the particulate catalysts of the different sizes prepared in the above (2-1). A total of 10 experiments were conducted. In each of the experiments, synthesis gas was manufactured by causing mixture gas containing town gas ($CH_4/C_2H_6/C_3H_8/C_4H_{10}$=89.5/6.0/2.8/1.6) and oxygen at an O/C ratio of between 0.9 and 1.0 to flow through each of the catalyst layers at temperature of 250° C. under variable pressure and at variable flow velocity. Table 3 shows the conditions of the experiments. With regard to Table 3, the average particle size d was measured by observing the particle size of each of the particles contained in each of the particulate catalysts through a microscope and the arithmetic average of the observed particle sizes was adopted. The porosity of each of the catalyst layers was actually measured to find that it was 0.64 for A) and 0.6 for B). The gas flow velocities were determined by using these values.

(2-3) Results

Table 4 summarily shows the results of the experiments.

TABLE 3

| RUN No. | Skeleton diameter d (mm) | Gas flow velocity u (m/s) | Average density ρ (kg/m³) | Average viscosity μ (μPa · s) | Re Number ρud/μ (—) | Reaction area (cm²) |
|---|---|---|---|---|---|---|
| 1 | 0.39 | 0.56 | 1.67 | 29.02 | 12.53 | 1.7 |
| 2 | 0.39 | 1.35 | 1.68 | 29.04 | 30.33 | 1.7 |
| 3 | 0.39 | 0.49 | 2.34 | 29.03 | 15.50 | 1.7 |
| 4 | 0.39 | 0.49 | 3.34 | 29.02 | 21.77 | 1.7 |
| 5 | 0.39 | 0.60 | 3.70 | 29.50 | 29.58 | 1.7 |
| 6 | 1.02 | 1.11 | 0.34 | 29.05 | 13.03 | 1.7 |
| 7 | 1.02 | 2.46 | 0.34 | 29.05 | 28.94 | 1.7 |
| 8 | 1.02 | 0.49 | 1.68 | 29.05 | 28.94 | 1.7 |
| 9 | 1.02 | 0.29 | 3.27 | 28.88 | 33.59 | 1.7 |
| 10 | 1.02 | 0.41 | 3.29 | 28.91 | 47.94 | 1.7 |

TABLE 4

| RUN No. | Carbon conversion ratio 20 min after start of reaction % | Reaction time (h) | Carbon conversion ratio after elapse of reaction time (%) | Changing rate of conversion ratio (%/h) | stability |
|---|---|---|---|---|---|
| 1 | 80.1 | 19 | 80.1 | 0.00 | ○ |
| 2 | 82.3 | 17 | 81.6 | 0.04 | X |
| 3 | 81.1 | 92 | 80.1 | 0.01 | ○ |
| 4 | 79.7 | 50 | 75.0 | 0.09 | X |
| 5 | 86.7 | 17 | 84.8 | 0.11 | X |
| 6 | 82.0 | 1 | 82.0 | 0.00 | ○ |
| 7 | 80.2 | 1 | 79.0 | 1.21 | X |
| 8 | 78.9 | 150 | 72.1 | 0.05 | X |
| 9 | 67.8 | 15 | 66.9 | 0.06 | X |
| 10 | 67.6 | 4 | 66.2 | 0.34 | X |

(2-4) Inventors' Comment

From Table 4, it can be seen that hot spots are formed and the reaction performance of the catalyst falls when the synthesis gas manufacturing process is run under the condition of a Re number greater than 20.

EXAMPLE 3

For this Example, a catalyst layer unit of a radial flow reactor was formed by using a cylindrical molded object of a foam catalyst having a cellular structure similar to that of Example 1. The structure of the catalyst layer unit 10 of a radial flow reactor illustrated in FIG. 3 is such that a gas feed pipe 11 is arranged at a position on the center axis of the cylindrical molded object of the catalyst having a predetermined radial thickness and mixture gas of source gas and oxidative gas supplied by way of the gas feed pipe 11 flows into the catalyst layer 12 through a plurality of gas permeation pores formed through the lateral wall of the gas feed pipe and flows further radially to cause synthesis gas to flow out from the outer surface of the catalyst layer. The catalyst layer is a foam molded object of about 10 to 40 cells/inch (4 to 16 cells/cm).

With the catalyst layer unit of a radial flow reactor, the gas introduced into the catalyst layer from the gas feed pipe flows and radially spreads. Therefore, the gas flow velocity is high near the gas feed pipe and gradually falls as the gas comes close to the outer surface of the catalyst layer unit if the volume change of the gas caused by the reaction that is in progress is disregarded. According to the present invention, an upper limit is provided for the Re number at the inlet of the catalyst layer. Therefore, in the instance of an In-Out type radial flow reactor, the Re number is less than the upper limit value in the entire area in the inside of the catalyst layer. Note, however, that, in actuality, an increase of the number of moles of gas and temperature changes will occur as the reaction proceeds in the catalyst layer, which affects the gas volume and yet the gas flow rate, so that the Re number may not necessarily be less than the upper limit in the entire area in the inside of the catalyst layer. Anyway, (because oxygen is gradually consumed,) hot spots are hardly formed in deep regions that are remote from the inlet of the catalyst layer and therefore what is most important here is to make the Re number not exceed the upper limit value of 20 at and near the inlet of the catalyst layer. For example, if the Re number somewhat exceeds the upper limit value at and near the outlet of the catalyst layer, the advantages of the present invention will not be lost immediately.

As pointed out above, in the instance of an In-Out type radial flow reactor, the Re number is made not to exceed the upper limit value at and near the inlet of the catalyst layer (near the gas feed pipe) where the gas flow velocity will generally show the highest value. Then, the gas flow velocity may become too low at and near the outlet of the catalyst layer particularly when the ratio of the outer diameter to the inner diameter of the catalyst layer is very large. If such is the case, a cylindrical layer of an inactive material having a predetermined thickness and gas flow paths similar to those of the catalyst layer may well be arranged around the gas feed pipe. When such a cylindrical layer of an inactive material is arranged, it is sufficient for the Re number not to exceed the upper limit value at the time when mixture gas passes through the layer of the inactive material and flows into the catalyst layer. With such an arrangement, therefore, when compared with an instance where no such a layer of an inactive material is arranged, the fall of the gas flow velocity at and near the outer surface of the catalyst layer (at the outlet side of the catalyst layer) will be significantly alleviated. In the instance of the arrangement of FIG. 3, the heat-insulating foam 13 takes the role of a layer of an inactive material. Such an arrangement of a layer of a heat-insulating material, which operates as an inactive material, makes it difficult for the heat generated in the catalyst layer to be transmitted to the inside of the gas feed pipe and hence is effective for prevention of ignition of mixture gas in the gas feed pipe. Additionally, when porous material having a small porosity is employed for the layer of an inactive material, an appropriate differential pressure is produced there to realize a uniform pressure distribution in the inside of the gas feed pipe. Then, gas is uniformly supplied to the catalyst layer in an effective manner across the entire length of the gas feed pipe between the front end and the tail end of the gas feed pipe.

While the radial flow reactor shown in FIG. 3 is of the In-Out type, where gas flows from the inside to the outside of the cylindrical catalyst layer, it may be replaced by an Out-In type radial flow reactor, where gas flows from the outside to the inside of a cylindrical catalyst layer.

EXAMPLE 4

In this Example, each catalyst layer unit was formed by arranging a plate-shaped (flat) molded object of a foam catalyst having a cellular structure similar to the foam catalyst of Example 1 and then arranging a gas feed plate and a gas collection plate at the opposite sides of the plate-shaped molded object so as to sandwich the plate-shaped molded object between them. Gas was made to flow in the thickness direction of the plate-shaped molded object. A plurality of such catalyst layer units were laid one above the other in the reactor of this Example and gas was made to flow in parallel. FIG. 4 is a schematic cross sectional view of part of the laminate of the catalyst layer unit of the plate-shaped reactor of this Example. Referring to FIG. 4, each of the catalyst layer units 20 includes a plate-shaped foam catalyst layer 21, a pair of heat-insulating foam layers 22 (inflow side layer 22a and outflow side layer 22b) made of a gas permeable inactive material and arranged to vertically sandwich the foam catalyst layer 21 between them and a support frame 23 for integrally holding the above listed layers. The support frame 23 by turn includes highly thermal shock-resistant and highly heat-insulating horizontal members 23a and vertical members 23b and 23c supporting the horizontal members 23a. The vertical members 23b and 23c are provided with slits, each of which operates either as a gas flow inlet for allowing gas to flow in from or as a gas flow outlet for allowing gas to flow out to one of the gaps, which will be described in detail hereinafter.

Note that, the reactor shown in FIG. 4 is designed to cause gas to flow vertically in the pressure vessel. The plate-shaped catalyst layer units are arranged horizontally and laid vertically one above the other. Therefore, the members that are arranged horizontally in FIG. 4 are referred to as horizontal members, while the members that support the horizontal members are referred to as vertical members. However, the catalyst layer units may not necessarily be arranged in the direction shown in FIG. 4 and hence the denominations of horizontal members and vertical members may be appropriately defined according to the direction in which the catalyst layer units are arranged.

The catalyst layer units are laid one above the other but any adjacently located ones are separated from each other by a predetermined gap such that mixture gas is allowed to flow in through one of the gaps located at the vertically opposite sides of each of the catalyst layer units while synthesis gas is allowed to flow out through the other gap. As the gaps for allowing gas to flow in, or gas inflow gaps, and the gaps for allowing gas to flow out, or gas outflow gaps, are arranged alternately, each of the gaps is advantageously shared by the pair of catalyst layer units sandwiching the gap.

The mixture gas that flows into the reactor then flows vertically downward from above along one of the vertical members having (normally a plurality of) slits and subsequently into the gas inflow gaps. Then, the gas flows horizontally through the gaps and penetrates into the catalyst layers so as to be converted into synthesis gas as it passes vertically through the catalyst layers. After departing from the catalyst layers, the synthesis gas flows horizontally through the gas outflow gaps and then passes through the slits that are designed to operate as gas outlets connected to the gas outflow gaps. Thereafter, the synthesis gas flows vertically downward from above along the other vertical member having those slits and goes out of the reactor.

Figure 7:
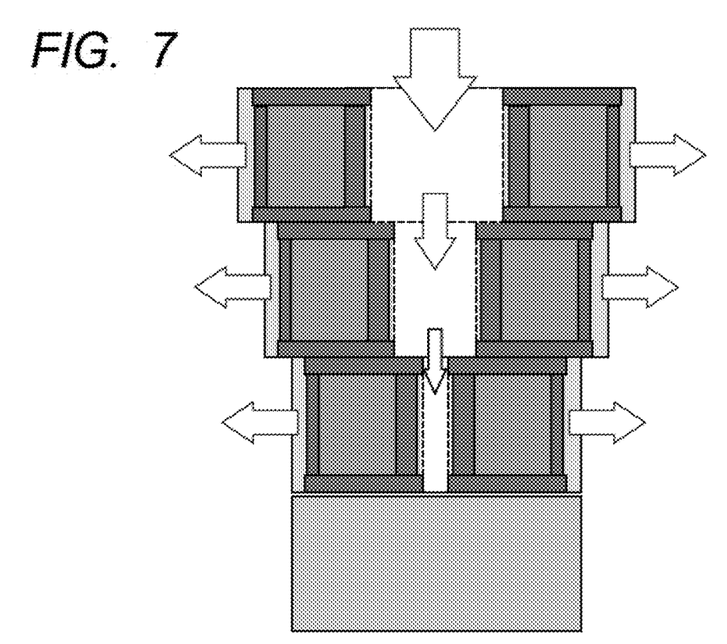
FIG. 7 is a schematic illustration of a mixture gas flow path arranged to stepwise reduce the width thereof.

When a plurality of catalyst layer units are arranged one above the other as shown in FIG. 4, mixture gas (source gas) that flows in the direction in which the catalyst layer units are arranged one above the other is then made to flow into the gas inflow gaps from the slits arranged along the flow path. Therefore, the flow rate of gas that flows through the gas flow path gradually falls from the upstream side toward the downstream side. Thus, if the gas flow path has a uniform width, the flow velocity of mixture gas gradually falls from the upstream side toward the downstream side to consequently increase the risk of explosion of mixture gas. To void this risk, the mixture gas flow path may well be made to have a width that gradually decreases from the upstream side toward the downstream side. FIG. 7 is a schematic illustration of a mixture gas flow path arrangement designed to reduce the width of the mixture gas flow path stepwise from the upstream side toward the downstream side. The flow path width may be reduced stepwise as shown in FIG. 7 or, alternatively, may be reduced continuously. When the flow path width is reduced stepwise, it is most rational that the width is reduced each time it passes by a slit position, although the present invention is by no means limited to such an arrangement.

Figure 8:
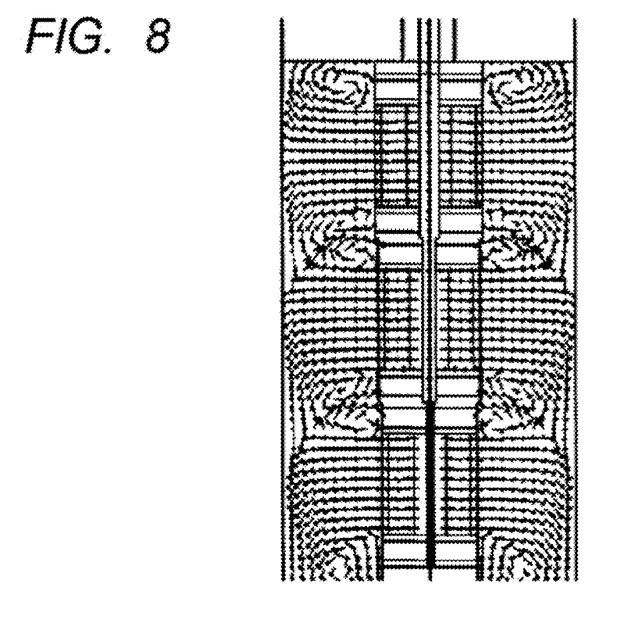
FIG. 8 is a schematic illustration of the flow velocity distribution in the catalyst layer of the catalyst layer unit of a plate reactor.

Meanwhile, in the case of the catalyst layer units of a plate reactor as shown in FIG. 7, the gas flow that passes through the catalyst layers actually includes not only a vertical flow component (flow component in the direction perpendicular to the gas inflow/outflow gaps) but also a horizontal flow component (component in the direction horizontal to the gas inflow/outflow gaps). The inventors of the present invention executed a computer simulation on the flow velocity distribution in the catalyst layers of the catalyst layer units of a plate reactor. FIG. 8 schematically illustrates the obtained results. As shown in FIG. 8, in the instance of the catalyst layer units of a plate reactor, the gas that flows in through the gas inflow gaps penetrates into the catalyst layers from the gas passage pores of the gas distribution plates under its own pressure and then into the gas outflow gaps through the gas passage pores of the gas collection plates arranged at the opposite side. Uniform pressure is realized in the gas inflow gaps and gas is ideally introduced into the catalyst layers in vertical flows relative to the catalyst layers by arranging ceramic porous members that produce appropriate differential pressure at the gas distribution plate side of the respective catalyst layers. It is necessary to select appropriate operating conditions so as to make the Re number at the inlets of the catalyst layers not exceed the upper limit value. A uniform gas flow is also realized in the inside of the catalyst layers by arranging ceramic porous members that produce appropriate differential pressure also at the outlet side of the catalyst layers. While FIG. 8 shows the results of a computer simulation designed to employ a plate reactor, it is also necessary to select appropriate operating conditions so as to make the Re number at the inlets of the catalyst layers not exceed the upper limit value when an Out-In type radial flow reactor or an In-Out type radial flow rector is employed.

Thus, formation of hot spots can be prevented by appropriately selecting the operating conditions so as to make the Re number not exceed the upper limit value at the inlets of the catalyst layers in a manner as described above. On the other hand, the gas flow velocity in the gas feed line needs to be made greater than the critical burning velocity thereof to prevent mixture gas flowing into the catalyst layers from exploding. Generally, an In-Out type radial flow reactor in which the gas flow velocity at the inlet side of the catalyst layers can be made high or a plate reactor in which the cross sectional area of the flow paths can be reduced stepwise when a plurality of plate-shaped catalyst layer units are sequentially arranged from the upstream side toward the downstream side is preferable from the viewpoint of designing a reactor that can prevent formation of hot spots and explosion of mixture gas entering the catalyst layers. As described earlier, the expression of "critical burning velocity" as used herein refers to the lowest gas flow velocity necessary to cause flame quenching (blow off). The critical burning velocity depends on the propagation speed of flames, or the speed of combustion reaction, and hence on the pressure and the temperature and also on the pipe diameter, the reacting gas species and the composition such as oxygen/carbon ratio. Generally, natural gas contains methane as main component and hence, when source gas is methane and the pipe diameter is 15 mm, the critical burning velocity with, for example, $CH_4/O_2=2/1$, 1.5 MPa (gauge pressure) and 0° C., which are reaction conditions for CPDX, is about 1.0 m/s. Therefore, it is sufficient for the flow velocity of the supplied mixture gas in the gas feed line to be not less than 1.0 m/s. Furthermore, when the throughput per unit time is predetermined for the supplied gas, it is necessary to select a catalyst cross sectional area (reaction area) that makes the Re number not exceed 20 at the catalyst inlet so that no hot spots may be formed on the catalyst surface, select the size of radial flow reactor or plate reactor to be used so as to make the reactor have such a catalyst cross sectional area and determine the gas feed line diameter or the slit width that makes the gas flow velocity in the gas feed line not less than the critical burning velocity. The use of equivalent diameter is recommended when determining the slit width. In radial reactors and plate reactors, the flow velocity of feed gas becomes the lowest at the tail end of the gas feed line and feed gas flows only in the direction vertical to the catalyst surface. This flow velocity is determined to be within the range that makes the Re number not exceed 20 at the catalyst layer inlet. For example, in the instance of the conditions shown in Table 1 for RUNS, the flow velocity is 0.91 m/s at the catalyst layer inlet. Under the conditions, the gas linear velocity in the gas feed pipe falls down to as low as 0.26 m/s when reduced to 0° C. Thus, explosion at the tail end of the gas feed line can be avoided by designing reaction conditions or the gas feed line diameter or the slit width so as to make the critical burning velocity lower than 0.26 m/s at 0° C.

EXAMPLE 5

The critical burning velocity $V_0$ that is required for embodying in the present invention is determined firstly by determining the velocity gradient (extinction strain rate) K (unit $s^{-1}$) at the time of blow off for counter flow flames by means of reaction analysis software (such as Chemkin) and then determining it as gas flow velocity V (unit m/s) that satisfies the requirement of the formula shown below.

$$K=2V/R \quad (2)$$

In the above formula, R is the counter flow interval (unit m). The counter flow interval is equivalent to the diameter of the cylindrical pipe when the flow is in a cylindrical pipe, whereas it is equivalent to the gap width when the flow is in a gap between flat plates. This will be referred to as equivalent diameter R hereinafter. Burning in the feed flow path (flame propagation) can be prevented from taking place by determining the value of the extinction strain rate K in advance under various conditions (temperature, pressure, gas composition, etc.) for calculations and selecting an equivalent diameter R that does not make the gas flow velocity $V_1$ in the feed flow path fall below the critical burning velocity $V_0$. Note that the gas flow velocity $V_1$ in the feed flow path is given by the formula (3) shown below:

$$V_1=4F/\pi R^2 \quad (3),$$

where F is the feed gas flow rate ($m^3/s$).

As pointed out above, the requirement to be met to prevent burning in the feed flow path is $V_0 \leq V_1$ and hence the conditional formula (4) shown below is led out from this requirement and the formulas (2) and (3). In other words, the equivalent diameter R of the feed flow path may well be selected so as to satisfy the requirement of the formula (4).

$$R \leq (8F/\pi K)^{1/3} \quad (4)$$

Figure 9A:
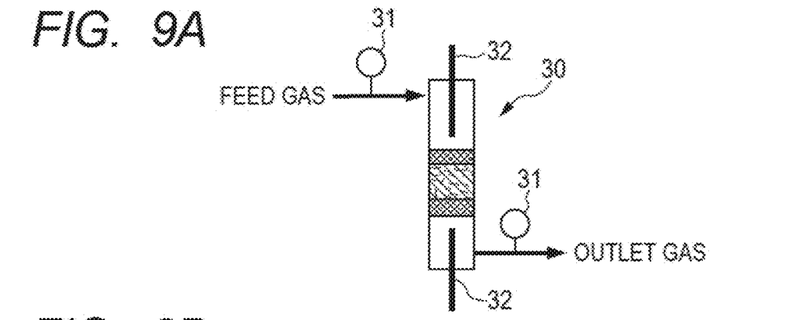
FIG. 9A is a schematic illustration of the tubular reactor employed in an experiment for seeing the relationship between the gas feed velocity and appearance or non-appearance of flame propagation.
Figure 9B:
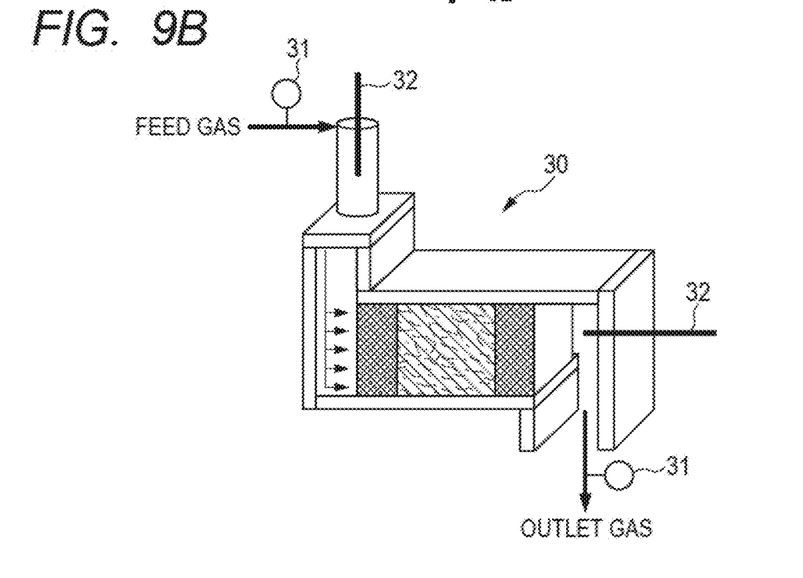
FIG. 9B is a schematic illustration of the plate-shaped reactor having slit-like feed paths employed in an experiment for seeing the relationship between the gas feed velocity and the appearance or non-appearance of flame propagation.

The inventors of the present invention looked into the influence of the magnitude relationship between the gas flow velocity and the critical burning velocity in a feed flow path on the occurrence or non-occurrence of flame propagation by using apparatus as shown in FIGS. 9A and 9B. The apparatus shown in FIG. 9A is an apparatus for forming a tubular reactor and the apparatus shown in FIG. 9B is an apparatus for forming a plate reactor having slit-like feed paths. Gas heated to a predetermined temperature (250 to 300° C.) and having a predetermined composition ($CH_4/O_2=2$) is fed to the apparatus 30 shown in FIG. 9A or the apparatus 30 shown in FIG. 9B and the pressure is raised to examine the occurrence or non-occurrence of flame propagation (appearance of flames after ignition) at the gas inflow gap. The gas pressure and the gas temperature were measured both at the inlet side and at the outlet side respectively by means of pressure gauges 31 and thermocouples 32. An occurrence of flame propagation was decided when the feed gas temperature and the feed gas pressure rose abruptly. Table 5 summarily shows the obtained results.

TABLE 5

| RUN No. | Shape | Equivalent diameter/mm | Feed gas linear velocity/m/s | Critical burning velocity/m/s | Occurrence of flame propagation |
|---|---|---|---|---|---|
| 1 | slit | 4.6 | 0.07 | 0.12 | yes |
| 2 | slit | 4.6 | 0.06 | 0.05 | no |
| 3 | cylinder | 16.0 | 0.14 | 0.68 | yes |
| 4 | cylinder | 16.0 | 0.19 | 0.18 | no |
| 5 | cylinder | 9.0 | 0.39 | 0.67 | yes |
| 6 | cylinder | 9.0 | 0.40 | 0.28 | no |

As seen from the results of RUN 1, 3 and 5, flame propagation was confirmed when the gas feed flow velocity is lower than the critical burning velocity. To the contrary, as seen from the results of RUN 2, 4 and 6, it was confirmed that no flame propagation took place and flames are blown off when the gas feed flow velocity is higher than the critical burning velocity.

Figure 10:
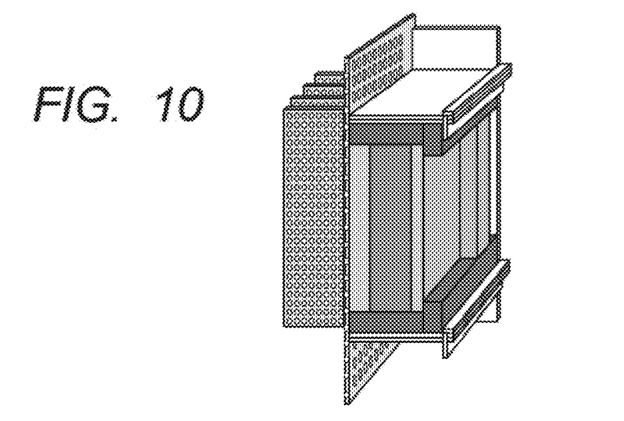
FIG. 10 is a schematic illustration of an arrangement in the inside of a mixture gas flow path where a metal plate having punched holes is disposed.

Thus, according to the present invention, it is possible to avoid explosion of mixture gas by selecting and defining operating conditions that make the mixture gas flow velocity not lower than the critical burning velocity within the range of Re number in the catalyst layers not exceeding 20. However, if it is difficult to select and define such conditions, explosion of mixture gas can be prevented by arranging a filler substance having a flame quenching effect in the mixture gas flow path as described in Patent Literature 4 with priority given to prevention of formation of hot spots. In such an instance, if the packing density of the filler substance is too high, the pressure loss due to the too high packing density may undesirably become too large. A technique of arranging a plurality of metal plates having punched out holes (punched metal plates) can be employed to provide a high flame quenching effect (explosion prevention effect) if the packing density is low. FIG. 10 is a schematic illustration of such punched metal plates arranged in the mixture gas flow path. As a result of arranging the punched metal plates, the equivalent diameter of the mixture gas flow path is reduced and accordingly, the critical burning velocity of the mixture gas flowing through the punched metal plates is reduced, so that an explosion prevention effect can be expected without excessively raising the mixture gas flow velocity. Note, however, that punched metal plates are not the only filler substance that provides a flame quenching effect (explosion prevention effect) and porous plates, which may be made of metal networks or sintered metal, or inactive monolithic ceramic objects or alumina beads that do not carry any catalyst may alternatively be employed.

Note that the risk of explosion is reduced by making the temperature of the mixture gas in the feed gas flow path lower than the self-ignition temperature of the mixture gas. Then, additionally, any side reaction in the vapor phase is suppressed to improve the selectivity for synthesis gas. Furthermore, production of substances such as tar and/or carbon that can eventually block the flow path is also suppressed.

EXAMPLE 6

This example is a synthesis gas manufacturing apparatus designed to operate with a catalytic partial oxidation method and comprise a mixture mechanism for mixing source gas containing lower hydrocarbons and oxidative gas containing oxygen is arranged at the upstream side of the catalyst layers such that the mixture gas from the mixing mechanism is forced to flow through the catalyst layers, which may be those of any of Examples 1 through 4.

While any mixing mechanism may be used for this example so long as it can mix gases of two different types, the use of a compact mixing mechanism that can be arranged within the reactor is preferable. Preferably, such a compact mixing mechanism is arranged near the inlet of the catalyst layers so that the mixture gas produced from the mixing mechanism may immediately be led into the catalyst layers. The mixture gas that is thoroughly mixed in and produced from the mixing mechanism is apt to explode. This is because if the flow path from the mixing mechanism to the inlets of the catalyst layers is long, there can be instances where it is difficult to make the flow velocity of the produced mixture gas higher than the critical burning velocity thereof and the flame quenching structure for preventing explosion can require a long distance for installation. In the instance of a plate reactor, preferably the mixing mechanism is so arranged that the mixture gas produced from the mixing mechanism flows straight into the flat-shaped gas flow path from the gas feed path as a flow running in parallel with the catalyst layers.

This application claims the benefit of Japanese Patent Application No. 2015-059106, filed on Mar. 23, 2015, which is incorporated herein by reference in its entirety.

REFERENCE SIGNS LIST

10: catalyst layer unit
11: gas feed pipe
12: catalyst layer
13: heat-insulating foam
20: catalyst layer unit
21: foam catalyst layer
22: heat-insulating foam layer
23: support frame
30: reactor
31: pressure gauge
32: thermocouple

The invention claimed is:

1. A method of manufacturing synthesis gas by catalytic partial oxidation, comprising causing mixture gas of source gas containing lower hydrocarbons and oxidative gas containing oxygen to flow through a fixed bed catalyst layer in a reactor and thereby converting the mixture gas into synthesis gas containing hydrogen and carbon monoxide as main components thereof, characterized in that the mixture gas is caused to flow through the catalyst layer under a condition where the Reynolds number does not exceed 20 at the inlet of the catalyst layer.

2. The method according to claim 1, wherein the gas flow velocity of the mixture gas in a mixture gas feed flow path reaching to the catalyst layer is not less than the critical burning velocity.

3. The method according to claim 1, wherein the temperature of the mixture gas is lower than the self-ignition temperature of the lower hydrocarbons at the inlet of the catalyst layer.

4. The method according to claim 1, wherein the mixture gas is obtained by separately introducing the source gas and the oxidative gas into a mixing vessel and then mixing the source gas and the oxidative gas in the mixing vessel.

5. The method according to any claim 1, wherein the lower hydrocarbons comprise methane.

6. The method according to claim 1, wherein the oxidative gas contains oxygen by 20 to 99.9 mol %.

* * * * *